(12) United States Patent
Chen

(10) Patent No.: US 11,285,519 B2
(45) Date of Patent: Mar. 29, 2022

(54) AUTOMATIC DISINFECTION DEVICE FOR VR SELF-SERVICE MACHINE

(71) Applicant: VR LEO USA, INC., Los Angeles, CA (US)

(72) Inventor: Xiuchao Chen, Shanghai (CN)

(73) Assignee: VR LEO USA, INC., Los Angeles, CA (US)

( * ) Notice: Subject to any disclaimer, the term of this patent is extended or adjusted under 35 U.S.C. 154(b) by 375 days.

(21) Appl. No.: 16/572,940

(22) Filed: Sep. 17, 2019

(65) Prior Publication Data

US 2020/0086361 A1     Mar. 19, 2020

(51) Int. Cl.
*B08B 7/00*         (2006.01)
*A61L 2/10*         (2006.01)
*G06F 3/0338*       (2013.01)

(52) U.S. Cl.
CPC .............. *B08B 7/0057* (2013.01); *A61L 2/10* (2013.01); *G06F 3/0338* (2013.01); *A61L 2202/11* (2013.01); *B08B 7/0035* (2013.01)

(58) Field of Classification Search
CPC ...... A61L 2/10; A61L 2202/11; B08B 7/0057; G06F 3/0338
See application file for complete search history.

(56) References Cited

U.S. PATENT DOCUMENTS

2018/0093001 A1 *   4/2018   Georgeson ................ A61L 2/24

* cited by examiner

*Primary Examiner* — Sean E Conley
(74) *Attorney, Agent, or Firm* — M.J. Ram and Associates

(57) ABSTRACT

The present utility model discloses an automatic disinfection device for a VR self-service machine, which is composed of two parts, a head display disinfection device and a joy stick disinfection device. The head display disinfection device comprises a light tube fixing base, a disinfecting light tube, a fixing bolt and a power line. The disinfection light tube installed on two sides of an inner wall of a VR self-service head display storage device. The joy stick disinfection device comprises a disinfecting light bulb installed under the back plate of a VR self-service machine through a back plate attachment, the and a protective cover is installed in front of the disinfecting light bulb.

2 Claims, 4 Drawing Sheets

AUTOMATIC DISINFECTION DEVICE FOR VR SELF-SERVICE MACHINE

This application claims benefit of Chinese Patent Application No. 201821514354.8 filed Sep. 17, 2018.

TECHNICAL FIELD

The present utility model relates to a game device, in particular to automatic disinfection devices capable of disinfecting a VR head device and VR controllers which are a part of the game device.

BACKGROUND ART

In an unattended environment, an existing VR self-service machine has the problems that the head device and the one or more manually operated controllers, typically joy sticks have been used by many people and thus their sanitary conditions are very undesirable. In addition facial and hand bacteria are prone to cross infection, thereby affecting the user experience in some cases; the user may even reject the VR game and its high-quality game contents because of unsanitary conditions. As a result, the cost for providing users with a good VR game experience is increased, which affects the popularity of VR games as well as the promotion of the VR industry.

SUMMARY

In order to solve the above problems, the present embodiments provides a set of automatic disinfection solutions for the head display and the VR controllers, such as joy sticks, of a VR self-service machine, which can achieve automatic disinfection for the head display and the VR controllers in an unattended environment.

The technical solution adopted by the present embodiments to solve the above technical problems is an automatic disinfection device for a VR self-service machine comprising two parts: a head display disinfection device and a controller disinfection device.

The head display disinfection device comprises a light tube fixing base, a disinfecting light tube, a mounting structure such as a fixing bolt and a power line. In the embodiment shown, the disinfection light tube is fixed on the light tube fixing base, and is installed on both sides of an inner wall of a VR self-service head display storage device through a fixing bolt. The disinfection light tube emits an ultraviolet irradiation to the head display so as to disinfect the head display. This enables automatic disinfection of the head display in an unattended environment.

In the embodiment shown a joy stick disinfection device comprises a protective cover, a back plate attachment, and disinfecting light bulbs. The disinfecting light bulbs are installed under the back plate of a VR self-service machine through a back plate attachment, the protective cover is installed in front of the disinfecting light bulbs, and the joy stick is irradiated by the joy stick disinfecting device for disinfection (the UV light bulbs). This enables automatic disinfection of the joy stick in an unattended environment.

The beneficial effects of the present embodiments are that the automatic disinfection device for VR self-service machine has the advantages of simple operation, convenient use, no manual disinfection necessary on site, and the users can wear the disinfected head display and pick up the disinfected joy stick in a safe and hygienic manner. In this way, the VR device can be used in an unattended environment, which makes the operation simpler, more efficient, and lower in cost, thereby greatly reducing the threshold of entry to the VR entertainment industry.

BRIEF DESCRIPTION OF THE DRAWINGS

The present utility model is further described in detail below with reference to the accompanying drawings.

DETAILED DESCRIPTION OF THE EMBODIMENTS

The structure and components of the head display disinfecting device is described in detail below with reference to FIG. 1 and FIG. 2.

Figure 1:
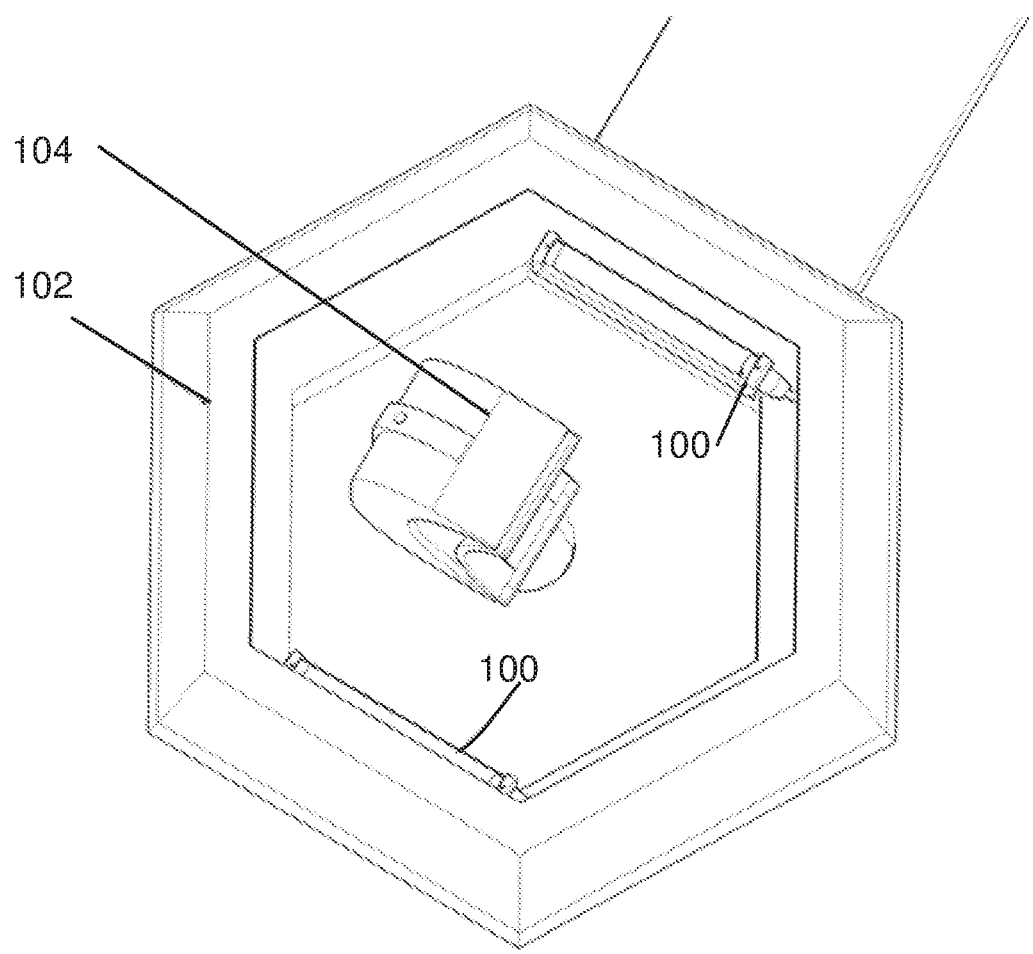
FIG. 1 is a bottom view of a head display of a VR self-service machine showing the installation position of the disinfection device.

As shown in FIG. 1, a pair of head display disinfection devices 100 are respectively installed on two sides of an inner wall of the head display storage device 102 so the head display disinfection devices 100 irradiates the head display 104 to disinfect the head display.

Figure 2:
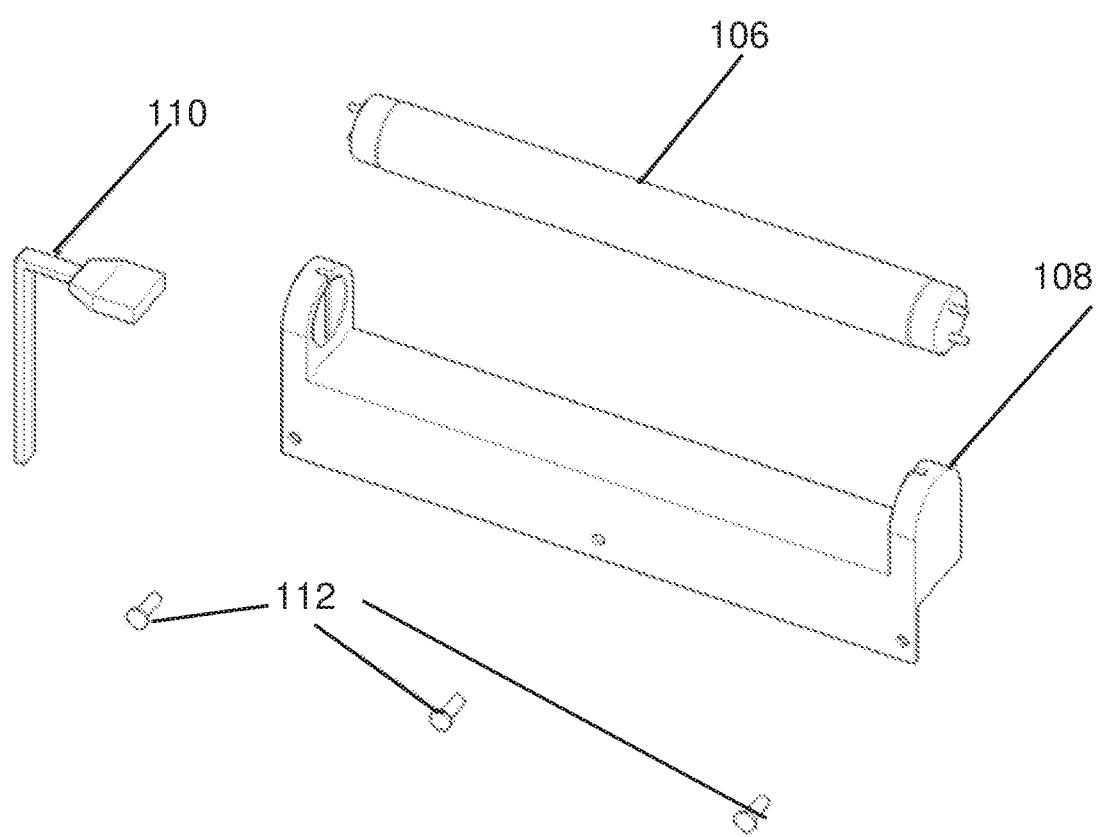
FIG. 2 is an exploded view of the head display disinfection device structure.

As shown in FIG. 2, the head display disinfection device 100 comprises a disinfecting light tube 106, a light tube fixing base 108, a power line 110, and a securing devices 112 such as bolts, screws or mounting structures for removably attaching the securing head display disinfection device 100 to the inner wall of the head display storage device 102. The disinfecting light tube 106 is fixed on both sides of the inner wall of the head display storage device 102 through the light tube fixing base 108. The VR self-service host supplies power to the head display disinfection device 100 through the first power line 110.

When the VR self-service machine host is in a working state, the head display 104 is lowered from the head display storage device 102, and the VR self-service machine host stops supplying power to the head display disinfection devices 100, and the disinfection process is thus stopped. When the VR self-service machine host is not working, the head display 104 is automatically recycled to the head display storage device 102, and the VR self-service machine host starts to supply power to the head display disinfection devices 100, and the disinfection process thus begins.

The structure and components of the joy stick disinfecting device are described in detail below with reference to FIG. 3 and FIG. 4.

Figure 3:
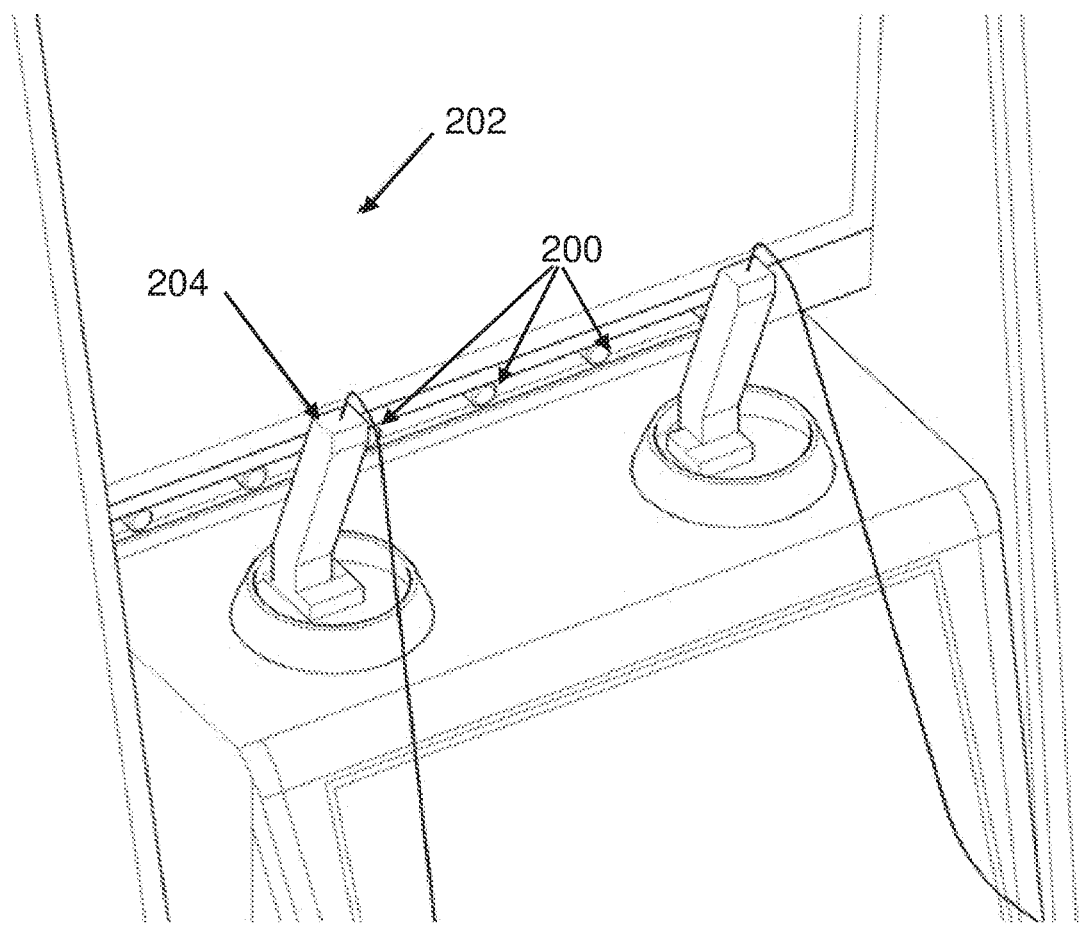
FIG. 3 is a view showing the installation position of a joy stick disinfection device on a VR self-service machine.

As shown in FIG. 3, the joy stick disinfection device 200 is installed under the back plate 202 so that the joy stick disinfection device 200 irradiates the joy stick 204 to disinfect the joy stick.

Figure 4:
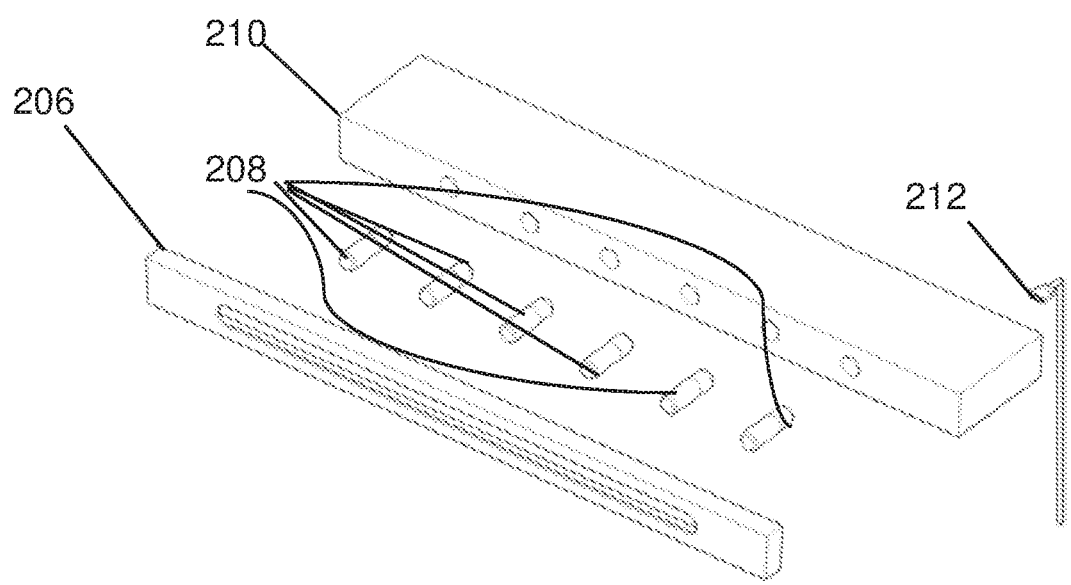
FIG. 4 is an exploded view of a joy stick disinfection structure incorporating features of the invention.

As shown in FIG. 4, the joy stick disinfection device 200 comprises a protective cover 206, disinfecting light bulbs 208, a back plate attachment 210, and a second power line 212. The disinfecting light bulbs 208 are installed in openings in a bulb base on the back plate attachment 210, the protective cover 206 is installed in front of the disinfecting bulb 208, and the VR self-service machine provides power to the joy stick disinfection device 200 through the second power line 212.

When the VR self-service machine host is in a working state, the power supply to the joy stick disinfection device 200 is turned off, thus the disinfection process is stopped. When the VR self-service machine host is not working, the joy stick is placed in a designated position of the VR self-service machine host, after a designated period of time, such as 5 minutes, the VR self-service machine supplies power to the joy stick disinfection device 200, and the disinfection process begins. If the machine is turned back on, the VR self-service machine stops supplying power to the joy stick disinfection device 200, and the disinfection process stops.

Various modifications and changes can be made to the present utility model by a person skilled in the art. Therefore, the present embodiment covers various modifications and changes that come within the scope of the appended claims or equivalents thereof.

The invention claimed is:

1. An improved VR self-service machine, wherein the improved VR self-service machine includes:
   a. a VR head display automatically removable from and returnable to a head display storage portion of the VR self-service machine and one or more manually operated controllers for operating the VR self-service machine,
   b. a head display disinfection device positioned in the head display storage portion of VR self-service machine, said head display disinfection device comprising one or more light tube fixing bases, a disinfecting light tube mounted in the one or more light tube fixing bases, securing devices for mounting the head display disinfection device to at least one wall of the head display storage device and a first source of electrical power in communication with the one or more disinfecting light tubes, and
   c. the one or more manually operated controllers for operating the VR self-service machine comprising VR controllers operatively connected to a user control portion of the VR machine, a storage portion adjacent the user control portion of the VR machine for receiving a VR controller disinfection device, said VR controller disinfection device comprising one or more disinfecting light bulbs, the disinfecting light bulbs installed in a receiving attachment in or under a back plate of the VR self-service machine, the disinfecting light bulbs positioned to focus disinfectant beams of light onto contact surfaces of the VR controllers.

2. The improved VR self-service machine of claim 1 wherein the VR controllers are joy sticks.

* * * * *